United States Patent

Müller et al.

[11] Patent Number: 6,156,778
[45] Date of Patent: Dec. 5, 2000

[54] AGENTS FOR CONTROLLING HARMFUL FUNGI

[75] Inventors: Ruth Müller, Friedelsheim; Herbert Bayer; Hubert Sauter, both of Mannheim; Karl Eicken, Wachenheim; Frank Wetterich, Mutterstadt; Eberhard Ammermann, Heppenheim; Gisela Lorenz, Neustadt; Siegfried Strathmann, Limburgerhof; Maria Scherer, Landau; Klaus Schelberger, Gönnheim; Bernd Müller, Frankenthal; Joachim Leyendecker, Ladenburg, all of Germany

[73] Assignee: BASF Aktiengesellschaft, Ludwigshafen, Germany

[21] Appl. No.: 09/242,729
[22] PCT Filed: Aug. 27, 1997
[86] PCT No.: PCT/EP97/04679
§ 371 Date: Feb. 22, 1999
§ 102(e) Date: Feb. 22, 1999
[87] PCT Pub. No.: WO98/08386
PCT Pub. Date: May 3, 1998

[30] Foreign Application Priority Data

Aug. 28, 1996 [DE] Germany ............... 19634771
Sep. 10, 1996 [DE] Germany ............... 19636752

[51] Int. Cl.⁷ .................. A01N 43/56; A01N 43/64; A01N 47/10
[52] U.S. Cl. .................. 514/383; 514/407; 514/478; 514/479
[58] Field of Search ............... 514/407, 383, 514/478, 479

[56] References Cited

U.S. PATENT DOCUMENTS

| | | | |
|---|---|---|---|
| 4,358,408 | 11/1982 | Krueger et al. | 260/453 |
| 5,210,084 | 5/1993 | Wollweber et al. | 514/237 |
| 5,491,165 | 2/1996 | Dehne et al. | 514/479 |
| 5,650,423 | 7/1997 | Dehne et al. | 514/376 |
| 5,869,517 | 2/1999 | Mueller et al. | 514/407 |

FOREIGN PATENT DOCUMENTS

| | | |
|---|---|---|
| 2225361 | 2/1997 | Canada . |
| 2227283 | 3/1997 | Canada . |
| 4321897 | 7/1993 | Germany . |
| 19528651 | 8/1995 | Germany . |
| 19531814 | 8/1995 | Germany . |
| 95/02115 | 1/1995 | WIPO . |
| 95/08636 | 3/1995 | WIPO . |
| 95/21153 | 8/1995 | WIPO . |
| 96/01258 | 1/1996 | WIPO . |
| 9601256 | 1/1996 | WIPO . |
| 96/07638 | 3/1996 | WIPO . |

OTHER PUBLICATIONS

Ingersoll et al. *J. Am. Chem. Soc.*, 58, 1936, 1808–11.
Ramalingam et al., *Ind. J. Chem.*, 10, 366, 1972.
Yamada et al. *Tetrahedron Letters*, 18, 1973, 1595–98.

Primary Examiner—Allen J. Robinson
Attorney, Agent, or Firm—Keil & Weinkauf

[57] ABSTRACT

This invention relates to a composition for controlling harmful fungi comprising, in a solid or liquid carrier,
a) at least one carbamate of the formula I

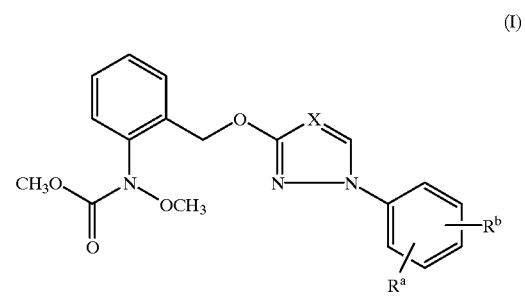

where
X is CH or N and
the radicals $R^a$ and $R^b$ independently of one another are a hydrogen atom, a halogen atom, a $C_1$–$C_4$-alkyl or a $C_1$–$C_4$-haloalkyl group; and
b) at least one valine amide of the formula II

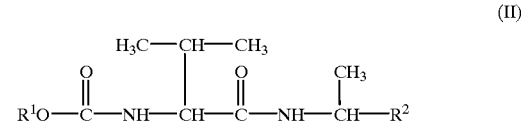

where
$R^1$ is $C_3$–$C_4$-alkyl and
$R^2$ is naphthyl or phenyl, the phenyl radical being substituted in the 4-position by a halogen atom, a $C_1$–$C_4$-alkyl group or $C_1$–$C_4$-alkoxy group.

11 Claims, No Drawings

AGENTS FOR CONTROLLING HARMFUL FUNGI

This application is a 371 of PCT/EP97/04679, filed Aug. 27, 1997.

The present invention relates to compositions for controlling harmful fungi, in particular to fungicidally active mixtures of certain carbamates or oxime ethers and valine amides. Moreover, the invention relates to a method of controlling harmful fungi using these compositions.

Compounds of the formula IIIa (IIIa)

in which $R^{11}$, $R^{12}$, $R^{13}$, $R^{14}$, $R^{15}$, m and n have various meanings and X is an oxygen or amine group, their preparation and their use for controlling harmful fungi or animal pests have been disclosed in WO-A-96/01256. Corresponding triazole derivatives are described in WO-A-96/01258.

The earlier German Patent Application DE-A-195 28 651 describes oxime ethers of the formula IIIb (IIIb)

where
X is O or NH,
Y is CH, CHO or NO,
Z is O, S, NH or, for example, N-alkyl,
and $R^a$, $R^b$ and $R^c$ may have a series of different meanings.
These compounds are used for controlling harmful fungi or animal pests. Compounds of the same type are also described in WO-A-95/21153 and WO-A-95/2115.

Moreover, the prior art describes a series of amino acid amide compounds and their use for controlling harmful fungi. In this context, reference may be made, for example, to EP-A-0 398 072, to WO-A-96/07638, to DE-A-43 21 897 and to the earlier German Patent Application DE-A-195 31 814.

For example, DE-A-195 31 814 describes valine amide derivatives of the formula IIIc

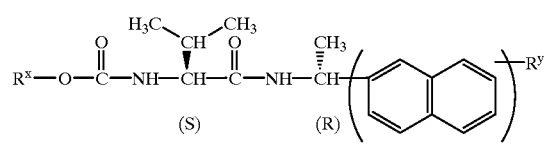

(IIIc)

in which $R^x$ and $R^y$ have various meanings and the two optically active centers are in the (S) and (R) configurations, respectively.

Furthermore, EP-A-0 610 764 discloses combinations of fungicidally active ingredients which comprise a valine amide derivative of the formula IIId

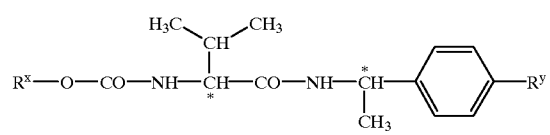

(IIId)

in which $R^x$ and $R^y$ have various meanings together with at least one further active ingredient selected from amongst dichlofluanid, tolylfluanid, chlorothalonil, propineb, thiram, mancozeb, dyrene, copper oxychloride, captan, dimetomorph, dithianon, phaltan, cymoxanil, propamocarb, fosetyl, metalaxyl, oxadixyl, fluazinam, methoxyacrylates, methoximinoacetates, furalaxyl, azoles, such as, for example, triadimenol, bitertanol, triadimefon and tebuconazole, etridiazole and pencycuron.

It is an object of the present invention to provide novel combinations of active ingredients for better control of harmful fungi. In particular, it is an object to provide those mixtures which are distinguished by a synergistic effect, thus allowing the rates of application of active ingredients employed to be reduced.

We have found that this object is achieved, surprisingly, by providing fungicidally active mixtures comprising, in a solid or liquid carrier, a) at least one compound of the formula I

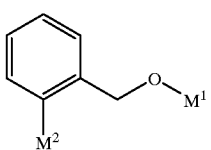

(I)

where
(a1) $M^1$ is a group of the formula

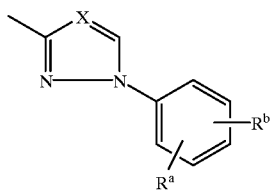

where
X is CH or N and
the radicals $R^a$ and $R^b$ independently of one another are a hydrogen atom, a halogen atom, a $C_1$–$C_4$-alkyl or a $C_1$–$C_4$kaloalkyl group; and
$M^2$ is a group of the formula

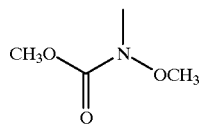

or
(a2) $M^1$ is a group of the formula

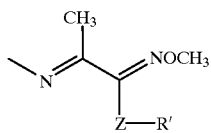

where
Z is O, S, NH or N—$C_1$–$C_4$-alkyl;
R' is $C_1$–$C_6$-alkyl, $C_1$–$C_6$-haloalkyl, $C_2$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; and
$M^2$ is a group of the formula

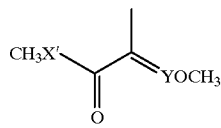

where
X' is O or NH; and
Y is CH or N;
and
b) at least one valine amide of the formula II

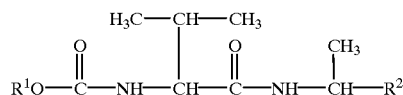

(II)

where
$R^1$ is $C_3$–$C_4$-alkyl and
$R^2$ is naphthyl or phenyl, the phenyl radical being substituted in the 4-position by a halogen atom, a $C_1$–$C_4$-alkyl or a $C_1$–$C_4$-alkoxy group.

Compositions of the present invention comprise as compounds of formula I in particular carbamates of the formula

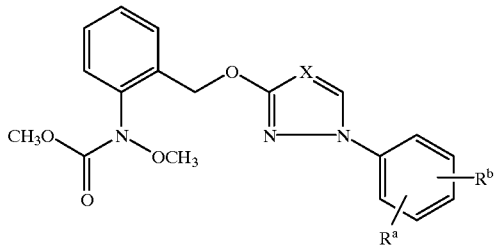

where X, $R^a$ and $R^b$ are as defined above
or
oxime ethers of the formula

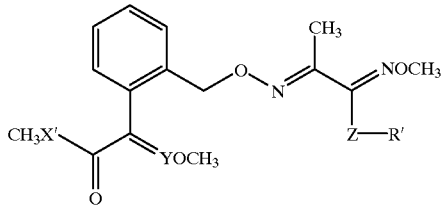

where X', Y, Z and R' are as defined above.

Surprisingly, it has been found, in particular, that better control of the harmful fungi is possible by applying the compounds of the formulae I and II jointly than when the individual compounds are used.

A combined use for the purposes of the present invention comprises the simultaneous or sequential use of the compounds according to the invention in any desired sequence. For the simultaneous use, the compounds may be applied jointly or separately from each other.

The abovementioned object is furthermore achieved by providing a method of controlling harmful fungi, which comprises treating the harmful fungi, their environment, or the plants, seeds, soils, areas, materials or spaces to be kept free from them, with an effective amount of a composition as defined above.

In the compounds used according to the invention, halogen is fluorine, chlorine, bromine or iodine, preferably fluorine, chlorine or bromine.

Examples of $C_1$–$C_4$-alkyl radicals are saturated straight-chain or branched hydrocarbon radicals having 1 to 4 carbon atoms, such as methyl, ethyl, n-propyl, 1-methylethyl, n-butyl, 1-methylpropyl, 2-methylpropyl, 1,1-dimethylethyl.

Examples of $C_1$–$C_4$-haloalkyl radicals are saturated straight-chain or branched hydrocarbon chains having 1 to 4 carbon atoms as defined above, it being possible for some or all of the hydrogen atoms in these groups to be replaced by halogen atoms such as, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2- dichloro-2-fluoroethyl, 2,2,2-trichloroethyl and pentafluoroethyl, 1-, 2- or 3-fluoropropyl, 1-, 2- or 3-chloropropyl; 1-fluoro- or 1-chlorobutyl.

Examples of $C_1$–$C_6$-alkyl radicals are saturated, straight-chain or branched hydrocarbon radicals having 1 to 6 carbon atoms, such as the examples given above for $C_1$–$C_4$-alkyl as well as pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Examples of $C_1$–$C_{20}$-alkyl radicals are saturated straight-chain or branched hydrocarbon radicals having 1 to 20 carbon atoms, for example $C_1$–$C_6$-alkyl radicals as mentioned above as well as longer chain alkyl radicals as straight-chain heptyl, octyl, nonyl, decyl, undecyl, lauryl, tridecyl, myristyl, pentadecyl, palmityl, heptadecyl, stearyl, nonadecyl, and arachinyl as well as single- or multiple-branched analogs thereof.

Examples of $C_1$–$C_6$-haloalkyl radicals are saturated straight-chain or branched hydrocarbon chains having 1 to 6 carbon atoms as defined above, where the hydrogen atoms in these groups can be partially or fully replaced by halogen atoms, such as the examples given above for $C_1$–$C_4$-haloalkyl as well as 1-fluoro- or 1-chloropentyl; 1-fluoro- or 1-chlorohexyl.

Examples of $C_2$–$C_6$-alkenyl radicals are unsaturated straight-chain or branched hydrocarbon radicals having 2 to 6 carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-1-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Examples of $C_2$–$C_6$-haloalkenyl radicals are straight-chain or branched hydrocarbon radicals having 2 to 6 carbon atoms and a double bond in any position as defined above, some or all of the hydrogen atoms being replaced by halogen atoms, for example 1-fluoro- or 1-chloroethenyl; 1-fluoro- or 1-chloro-1-propenyl, 1-fluoro- or 1-chloro-2-propenyl; 3-fluoro- or 3-chloro-2-propenyl, or 2,3,3-trichloro-2-propenyl.

Examples of $C_3$–$C_6$-alkynyl radicals are straight-chain or branched hydrocarbon groups having 3 to 6 carbon atoms and a triple bond in any position, such as 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Examples of $C_3$–$C_6$-haloalkynyl radicals are straight-chain or branched hydrocarbon groups having 3 to 6 carbon atoms and a triple bond in any position as defined above, some or all of the hydrogen atoms being replaced by halogen atoms, for example 3-fluoro- or 3-chloro-1-propynyl, 1-fluoro- or 1-chloro-2-propynyl.

Examples of $C_3$–$C_6$-cycloalkyl group include monocyclic alkyl groups having 3 to 6 carbon ring members, such as cyclopropyl, cyclobutyl, cyclopentyl and cyclohexyl.

Examples of $C_1$–$C_4$-alkoxy groups are straight-chain or branched alkyl radicals having 1 to 4 carbon atoms as defined above which are bonded to the molecule via an oxygen atom, for example methoxy, ethoxy, 1- or 2-propoxy and 1-butoxy.

Examples of $C_1$–$C_4$-haloalkoxy groups are straight-chain or branched alkoxy groups as defined above having 1 to 4 carbon atoms, where some or all of the hydrogen atoms may be replaced by halogen atoms, for example chloromethoxy, fluoromethoxy, 2-fluoro- or 2-chloroethoxy, 3-fluoro- or 3-chloropropoxy or 4-fluoro- or 4-chlorobutoxy.

Examples of $C_1$–$C_4$-alkylthio radicals are straight-chain or branched alkyl radicals having 1 to 4 carbon atoms as defined above which are bonded to the molecule via a sulfur atom, for example methylthio, ethylthio, 1- or 2-propylthio and 1-butylthio.

Preferred fungicidal compositions comprise oxime ethers of the formula IA or IB

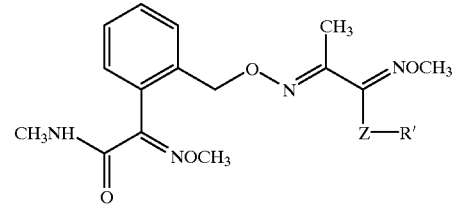

(IA)

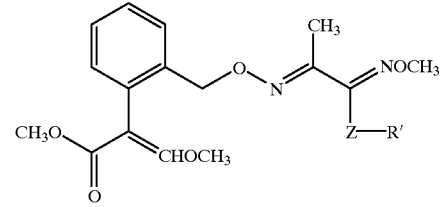

(IB)

where in each case
Z is O and
R' is $C_1$–$C_6$-alkyl, $C_1$–$C_6$-haloalkyl, $C_2$–$C_6$-alkenyl, $C_2$–$C_6$-haloalkenyl, $C_3$–$C_6$-cycloalkylmethyl, benzyl, or benzyl which is halogenated in the ring.

Especially preferred compounds of the formulae IA and IB are those whose radicals Z—R' have the meanings given in Table I below.

TABLE I

| No.         | ZR'                                                                    |
|-------------|------------------------------------------------------------------------|
| IA.1, IB.1  | O—CH$_2$CH$_2$CH$_3$                                                   |
| IA.2, IB.2  | O—CH(CH$_3$)$_2$                                                       |
| IA.3, IB.3  | O—CH$_2$CH$_2$CH$_2$CH$_3$                                             |
| IA.4, IB.4  | O—CH(CH$_3$)CH$_2$CH$_3$                                               |
| IA.5, IB.5  | O—CH$_2$CH(CH$_3$)$_2$                                                 |
| IA.6, IB.6  | O—CH(CH$_2$CH$_3$)CH$_2$CH$_3$                                         |
| IA.7, IB.7  | O—CH$_2$CH$_3$                                                         |
| IA.8, IB.8  | O—CH(CH$_3$)CH$_2$CH$_2$CH$_3$                                         |
| IA.9, IB.9  | O—CH$_2$C(CH$_3$)$_3$                                                  |
| IA.10, IB.10| O—CH$_2$CCl=CCl$_2$                                                    |
| IA.11, IB.11| O—CH$_2$CH=CH—Cl (trans)                                               |
| IA.12, IB.12| O—CH$_2$—C(CH$_3$)=CH$_2$                                              |
| IA.13, IB.13| O—CH$_2$-(cyclopropyl)                                                 |
| IA.14, IB.14| O—CH$_2$—C$_6$H$_5$                                                    |
| IA.15, IB.15| O—CH$_2$-[4-F—C$_6$H$_4$]                                              |

Examples of especially preferred compounds are IA.2 and IA.4. In the oxime ethers of the formula I, the C=Y— double bond can be present in the E or the Z configuration (in relation to the carboxylic acid function). However, the mixtures according to the invention may comprise the pure E or Z isomers or E/Z isomer mixtures. The E/Z isomer mixture or the E isomer is preferably used in each case, the E isomer of the oxime ether being especially preferred.

The C=N double bonds of the bisoxime ether side chain of the oxime ethers can also exist in the pure E or Z form or as E/Z isomer mixtures. However, both isomer mixtures and pure isomers, in relation to the C=N double bonds, can be used in the mixtures according to the invention. In particular, however, oxime ethers which have the following E/Z configuration in the side chain are preferred:

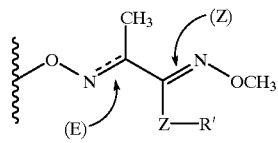

The oxime ethers of the formula I which are part of the compositions according to the invention and their preparation are known per se from the earlier German Patent Application DE-A-195 28 651, the entire contents of which are herewith referred to.

In accordance with this publication, oxime ethers of the formula I can be prepared, for example, by reacting a benzyl derivative of the formula IV

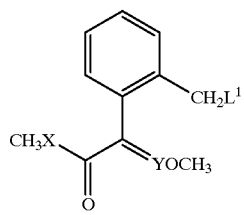

(IV)

where L$^1$ is a nucleophilically exchangeable leaving group, for example halogen or sulfonate groups, preferably chlorine, bromine, iodine, mesylate, tosylate and triflate, with a hydroxyimine of the formula v

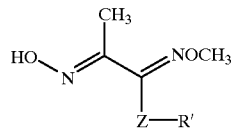

(V)

The reaction is carried out in a manner known per se in an inert organic solvent in the presence of a base (for example sodium hydride, potassium hydroxide, potassium carbonate and triethylamine) in accordance with the methods described in Houben-Weyl, 4th Ed., Vol. E 14b, p. 370 et seq. and Houben-Weyl, Vol. 10/1, p. 1189 et seq.

The hydroxyimine V required is obtained, for example, by reacting a suitable dihydroxyimine VI

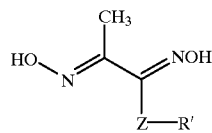

(VI)

with the nucleophilically substituted reagent H$_3$CL$^2$ where L$^2$ is a nucleophilically exchangeable leaving group, for example halogen or sulfonate groups, preferably chlorine, bromine, iodine, mesylate, tosylate and triflate.

The reaction is carried out in a manner known per se in an inert organic solvent in the presence of a base (for example potassium carbonate, potassium hydroxide, sodium hydride, pyridine and triethylamine) in accordance with the methods described in Houben-Weyl, Vol. E 14b, p. 307 et seq., p. 370 et seq. and p. 385 et seq.; Houben-Weyl, 4th Ed., Vol. 10/4, p. 55 et seq., p. 180 et seq. and p. 217 et seq.; Houben-Weyl, Vol. E 5, p. 780 et seq.

Those compounds of the formula VI which are not already known (DE-A-26 21 102) can be obtained by known methods.

Further preferred compositions comprise carbamates of formula IC

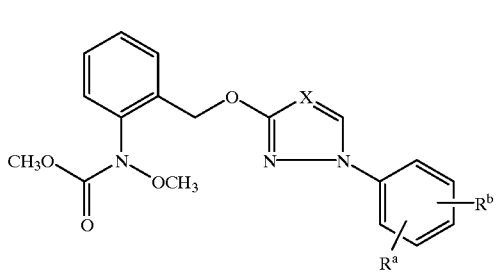

(IC)

where X has the abovementioned meaning and at least one of the radicals R$^a$ and R$^b$ is not a hydrogen atom and is, for example, selected from halogen and C$_1$–C$_4$-alkyl.

The carbamates applied according to the invention are known per se. Their preparation is described, for example, in WO-A-96/01256 and WO-A-96/01258, which are thus expressly referred to.

Examples which may be mentioned of preferred carbamates of the formula I are the compounds IC.1 to IC.52 listed in Table II below.

TABLE II

| No. | X | $R^a$ | $R^b$ |
|---|---|---|---|
| IC.1 | N | 2-F | H |
| IC.2 | N | 3-F | H |
| IC.3 | N | 4-F | H |
| IC.4 | N | 2-Cl | H |
| IC.5 | N | 3-Cl | H |
| IC.6 | N | 4-Cl | H |
| IC.7 | N | 2-Br | H |
| IC.8 | N | 3-Br | H |
| IC.9 | N | 4-Br | H |
| IC.10 | N | 2-$CH_3$ | H |
| IC.11 | N | 3-$CH_3$ | H |
| IC.12 | N | 4-$CH_3$ | H |
| IC.13 | N | 2-$CH_2CH_3$ | H |
| IC.14 | N | 3-$CH_2CH_3$ | H |
| IC.15 | N | 4-$CH_2CH_3$ | H |
| IC.16 | N | 2-$CH(CH_3)_2$ | H |
| IC.17 | N | 3-$CH(CH_3)_2$ | H |
| IC.18 | N | 4-$CH(CH_3)_2$ | H |
| IC.19 | N | 2-$CF_3$ | H |
| IC.20 | N | 3-$CF_3$ | H |
| IC.21 | N | 4-$CF_3$ | H |
| IC.22 | N | 2-F | 4-F |
| IC.23 | N | 2-Cl | 4-Cl |
| IC.24 | N | 3-Cl | 4-Cl |
| IC.25 | N | 2-Cl | 4-$CH_3$ |
| IC.26 | N | 3-Cl | 4-$CH_3$ |
| IC.27 | CH | 2-F | H |
| IC.28 | CH | 3-F | H |
| IC.29 | CH | 4-F | H |
| IC.30 | CH | 2-Cl | H |
| IC.31 | CH | 3-Cl | H |
| IC.32 | CH | 4-Cl | H |
| IC.33 | CH | 2-Br | H |
| IC.34 | CH | 3-Br | H |
| IC.35 | CH | 4-Br | H |
| IC.36 | CH | 2-$CH_3$ | H |
| IC.37 | CH | 3-$CH_3$ | H |
| IC.38 | CH | 4-$CH_3$ | H |
| IC.39 | CH | 2-$CH_2CH_3$ | H |
| IC.40 | CH | 3-$CH_2CH_3$ | H |
| IC.41 | CH | 4-$CH_2CH_3$ | H |
| IC.42 | CH | 2-$CH(CH_3)_2$ | H |
| IC.43 | CH | 3-$CH(CH_3)_2$ | H |
| IC.44 | CH | 4-$CH(CH_3)_2$ | H |
| IC.45 | CH | 2-$CF_3$ | H |
| IC.46 | CH | 3-$CF_3$ | H |
| IC.47 | CH | 4-$CF_3$ | H |
| IC.48 | CH | 2-F | 4-F |
| IC.49 | CH | 2-Cl | 4-Cl |
| IC.50 | CH | 3-Cl | 4-Cl |
| IC.51 | CH | 2-Cl | 4-$CH_3$ |
| IC.52 | CH | 3-Cl | 4-$CH_3$ |

The compounds IC.12, IC.23, IC.32 and IC.38 are especially preferred, in particular IC.32 and IC.38.

The compounds of the formula II as used according to the invention are also known per se. A first preferred group of valine amide derivatives are compounds of the formula II'

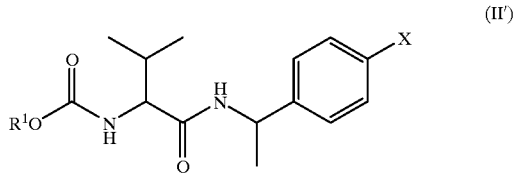

(II')

where $R^1$ is as defined above and X is halogen, $C_1$–$C_4$-alkyl or $C_1$–$C_4$-alkoxy. Compounds of this type and their preparation are described, for example, in EP-A-0 610 764 and EP-A-0 398 072, which are thus expressly referred to.

A further preferred group of valine amide derivatives are compounds of the formula II"

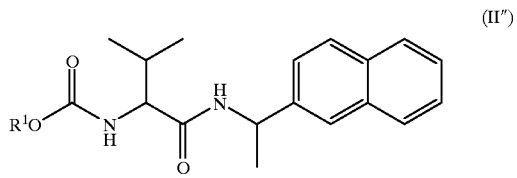

(II")

where $R^1$ is as defined above. Compounds of this type and their preparation are described, for example, in DE-A-43 21 897 and WO-A-96/07638, which are thus expressly referred to.

Preferred compounds of the formula II are those where $R^1$ is isopropyl, sec-butyl and tert-butyl.

Equally preferred compounds of the formula II are those where $R^2$ is α-naphthyl, β-naphthyl and phenyl, the phenyl being substituted in the 4-position by chlorine, bromine, $C_1$–$C_4$-alkyl or $C_1$–$C_4$-alkoxy.

Particularly preferred compounds of the formula II are those where $R^2$ is β-naphthyl, 4-chlorophenyl, 4-methylphenyl and 4-methoxyphenyl.

Preferred examples of valine amides which can be used in accordance with the invention are compiled in Table III below.

TABLE III

| No. | $R^1$ | $R^2$ |
|---|---|---|
| II.1 | isopropyl | β-naphthyl |
| II.2 | isopropyl | 4-chlorophenyl |
| II.3 | isopropyl | 4-methylphenyl |
| II.4 | isopropyl | 4-methoxyphenyl |
| II.5 | sec-butyl | β-naphthyl |
| II.6 | sec-butyl | 4-chlorophenyl |
| II.7 | sec-butyl | 4-methylphenyl |
| II.8 | sec-butyl | 4-methoxyphenyl |
| II.9 | tert-butyl | β-naphthyl |
| II.10 | tert-butyl | 4-chlorophenyl |
| II.11 | tert-butyl | 4-methylphenyl |
| II.12 | tert-butyl | 4-methoxyphenyl |

The compounds II.1, II.2 and II.9 are especially preferred, in particular II.1 and II.2.

The structural formula of the compounds of formula II shows that these compounds have two asymmetrically substituted carbon atoms. The compounds can therefore be used in the mixture according to the invention either as mixtures of various isomers or as pure isomers.

According to a further preferred embodiment, compounds of the formula II are used where the amino acid moiety is formed by alkoxycarbonyl-L-valine (S configuration) and the phenethylamine moiety or the naphthylethylamine moiety has the R configuration. Such compounds can be described by the formula IIa

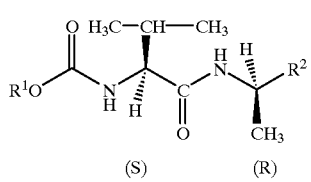

where $R^1$ and $R^2$ have the meanings mentioned for the compounds of the formula II.

The preferred isomers of the formula IIa are prepared by methods similar to those described in the earlier German Patent Application DE-A-195 31 814. Thus, the disclosure of this application is expressly referred to.

The isomerically pure compounds of the formula IIa can be prepared in a manner known per se starting from the corresponding carbamoylcarboxylic acids VII, which are based on L-valine. For example, the compounds IIa are obtained by the processes described hereinbelow, where a carbamoylcarboxylic acid VII is employed together with an amine VIII (the references "Houben-Weyl" refer to: Houben-Weyl, Methoden der Organischen Chemie [Methods in Organic Chemistry], 4th Edition, Thieme Verlag, Stuttgart):

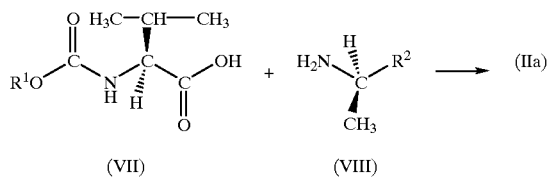

The carbamoylcarboxylic acids VII are known or can be prepared by known methods, mainly starting from the amino acid L-valine (cf. "Houben-Weyl", Volume 15/1, pp. 46–305, mainly pp. 117–125).

The amines VIII are also known or can be obtained readily (cf. Organikum [Organic Chemistry], VEB Deutscher Verlag der Wissenschaften, 15th Edition, Berlin, 1977, p. 610 et seq.; "Houben-Weyl", Volume 15/1, pp. 648–665; Indian J. Chem. 10, p. 366 (1972); J. Am. Chem. Soc. 58, (1936), pp. 1808–1811).

The R isomers can be separated from the racemates of the amines VIII in a manner known per se, for example by fractional crystallization with optically active tartaric acid or, preferably, by means of enzyme-catalyzed esterification and subsequent hydrolysis (cf., for example, WO-A-95/08636).

This process is preferably carried out in such a way that the carbamoylcarboxylic acids VII are first converted into carboxyl-activated derivatives, mainly into acyl cyanides or anhydrides (cf. Tetrahedron Letters, Volume 18, (1973), pp. 1595–1598, or "Houben-Weyl", Volume 15/1, pp. 28–32). These derivatives are then reacted with the amines VI in the presence of bases.

An example of a reaction which is suitable for the preparation of the carboxyl-activated acylcyanides is the reaction of the carbamoylcarboxylic acids VII with diethyl cyanophosphonate, mainly in an inert solvent such as tetrahydrofuran or toluene.

Preferred for the preparation of carboxyl-activated anhydrides is the reaction of the carbamoylcarboxylic acid VII with carbonic acid chlorides, such as isobutyl chloroformate, in the presence of bases and, if appropriate, in an inert solvent such as toluene or tetrahydrofuran.

The reaction of the amines VIII with the carboxyl-activated carbamoylcarboxylic acids VII is preferably carried out in a solvent such as dichloromethane, tetrahydrofuran or toluene.

The amines VIII may also act as the bases; they are normally recovered from the crude product.

In a preferred embodiment of this process step, the carbamoylcarboxylic acid VII, the amine VIII, the reagent which is suitable for producing the carboxyl-activated derivative of the carbamoylcarboxylic acid VII and the base are reacted in a one-pot process, if appropriate in an inert solvent, and the crude product is subsequently worked up in a manner known per se in order to isolate the carbamoylcarboxamide IIa.

Owing to their basic character, the compounds of the formulae I and II are capable of forming salts or adducts with inorganic or organic acids or with metal ions, which also may be used according to the invention.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth subgroup, in particular chromium, manganese, iron, cobalt, nickel, copper, zinc and others. Especially preferred are the metal ions of the elements of the subgroups of the fourth period. The metals can in this case be in the various valences which they can assume.

When preparing the mixtures, it is preferred to employ the pure active ingredients I and II, with which further active ingredients against harmful fungi or other pests such as insects, arachnids or nematodes, or else herbicides or growth-regulating active ingredients or fertilizers can be admixed, if required.

The mixtures of the compounds I and II, or the simultaneous, that is, joint or separate, use of the compounds I and II, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and cucurbits), barley, grass, oats, coffee, maize, fruit species, rice, rye, soybeans, grapevine, wheat, ornamentals, sugar cane, bananas and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on curcubits, *Podosphaera leucotricha* on apples, *Puccinia* species on cereals, *Rhizoctonia* species on cotton, rice and lawn, *Ustilago* species on cereals and sugar cane, *Venturia inaequalis* (scab) on apples, *Helminthosporium* species on cereals, *Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat and barley, *Pyricularia oryzae* on rice, *Phytophthora infestans* on potatoes and tomatoes, *Pseudoperonospora* species on cucurbits and hops, *Plasmopara viticola* on grapevines, *Alternaria* species on vegetables and fruit, *Mycosphaerella* species in bananas, and *Fusarium* and *Verticillium* species.

Furthermore, they can be used in the protection of materials (eg. in the protection of wood), for example against *Paecilomyces variotii*.

The compounds I and II are normally used in a weight ratio of from 10:1 to 0.1:1, preferably 5:1 to 0.2:1, in particular 5:1 to 1:1.

As non-limiting examples of useful anti-fungically active combinations of compounds there may be mentioned:

At least one compound of formula IA or IB and at least one compound of formula II, as for example compounds of Table I, like IA.2 or IA.4, each combined with compounds of Table III, like II.1.

At least one compound of formula IC and at least one compound of formula II, as for example compounds of Table II, like IC.32 or IC.38, each combined with compounds of Table III, like II.1 or II.2

The application rates of the mixtures according to the invention are from 0.01 to 3 kg/ha, preferably 0.1 to 1.5 kg/ha, in particular 0.1 to 1.0 kg/ha, depending on the nature of the desired effect.

In the case of the compounds I, the application rates are from 0.01 to 0.5 kg/ha, preferably 0.05 to 0.5 kg/ha, in particular 0.05 to 0.4 kg/ha.

Correspondingly, in the case of the compounds II, the application rates are from 0.01 to 0.5 kg/ha, preferably 0.05 to 0.5 kg/ha, in particular 0.05 to 0.4 kg/ha.

For seed treatment, the application rates of the mixture are generally from 0.001 to 50 g/kg seed, preferably 0.01 to 10 g/kg, in particular 0.01 to 8 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II, or of the mixture of the compounds I and II. The active ingredients are employed in a purity of from 90% to 100%, preferably 95% to 100% (according to NMR or HPLC spectrum).

The compounds I or II, or the mixtures, or the corresponding formulations, are applied by treating the harmful fungi or the plants, seeds, soils, areas, materials or spaces to be kept free from them with a fungicidally active amount of the mixture, or of the compounds I and II in the case of separate application. Application can be effected before or after infection by the harmful fungi.

Examples of the synergistic action of the mixtures according to the invention against harmful fungi The fungicidal activity of the compounds and of the mixtures was demonstrated by the following experiments:

The active ingredients, separately or together, were formulated as a 10% emulsion in a mixture of cyclohexanone and an emulsifier (as for example Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols)) and diluted with water to give the desired concentration.

Evaluation was carried out by determining the infected leaf areas in percent. These percentages were converted into efficacies. The expected efficacies of the mixtures of the active ingredients were determined using Colby's formula [R. S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B at concentrations of a and b x efficacy, expressed in % of the untreated control, when using the active ingredient A at a concentration of a y efficacy, expressed in % of the untreated control, when using the active ingredient B at a concentration of b The efficacy (W) was calculated as follows using Abbot's formula:

$$W = (1-\alpha) \cdot 100/\beta$$

α is the fungal infection of the treated plants in % and
β is the fungal infection of the untreated (control) plants in %

An efficacy of 0 means that the infection level of the treated plants corresponds to that of the untreated control plants; an efficacy of 100 means that the treated plants were not infected.

EXAMPLE 1

Action against Phytophthora infestans on tomatoes

The leaves of pot tomatoes of the variety "Große Fleischtomate" were sprayed until dripping wet with an aqueous suspension, which was prepared from a stock solution consisting of 10% active ingredient, 63% cyclohexanone and 27% emulsifier. The next day, these leaves were infected with an aqueous zoospore slurry of Phytophthora infestans. Then the plants were placed in a steam-saturated chamber at temperatures of from 16 to 18° C. Six days later, blight had developed on the untreated, but infected control plants to an extent allowing the visual determination of the infection in %.

The visually determined values for the percentage of leaf area infected were converted into efficacy values in % of untreated control. The efficacy values to be expected were calculated according to Colby's formula as described above.

| Active ingredient or mixture [conc.] | Efficacy in % of untreated control | efficacy (%) calculated according to Colby |
|---|---|---|
| untreated | 93% infection | — |
| IA.2 [5 ppm] | 5 | — |
| IA.4 [5 ppm] | 5 | — |
| II.1 [5 ppm] | 5 | — |
| IA.2 + II.1 [5 ppm] each | 40 | 9 |
| IA.4 + II.1 [5 ppm] each | 57 | 9 |

EXAMPLE 2

Action against *Plasmopara viticola*

The leaves of pot vines of the variety "Muller Thurgau" were sprayed until dripping wet with an aqueous suspension, which was prepared from a stock solution consisting of 10% active ingredient, 63% cyclohexanone and 27% emulsifier. In order to allow an evaluation of the permanent effect of these substances, the plants were placed in a greenhouse for 7 days upon drying of the spray coat, before their leaves were inoculated with an aqueous zoospore slurry of *Plasmopara viticola*. Then the vines were first placed in a steam-saturated chamber for 48 hours and then left in a greenhouse at temperatures of from 20 to 30° C. for 5 days. After this time, the plants were again placed in a humid chamber for 16 h in order to accelerate the outbreak of the sporangium carrier. Then, the degree of infection was visually determined on the undersurfaces of the leaves.

The visually determined values for the percentage of leaf area infected were converted into efficacy values in % of untreated control. The efficacy values to be expected were calculated according to Colby's formula as described above.

| Active ingredient or mixture [conc.] | Efficacy in % of untreated control | efficacy (%) calculated according to Colby |
|---|---|---|
| untreated | 93% infection | — |
| IC.32 [0.32 ppm] | 89 | — |
| IC.32 [0.08 ppm] | 25 | — |
| IC.38 [0.32 ppm] | 68 | — |
| II.1 [0.32 ppm] | 0 | — |
| II.2 [0.32 ppm] | 0 | — |
| II.2 [0.08 ppm] | 0 | — |
| IC.38 + II.1 [0.32 ppm] each | 95 | 68 |
| IC.32 + II.2 [0.32 ppm] each | 100 | 89 |
| IC.32 + II.2 [0.08 ppm] each | 46 | 25 |

The results reported in the above tables show that efficacies are obtained with the novel mixtures which are considerably higher than the efficacies calculated according to Colby's formula.

We claim:

1. A composition for controlling harmful fungi comprising, in a solid or liquid carrier, synergistically fungicidally effective amounts of
   a) at least one carbamate of the formula I

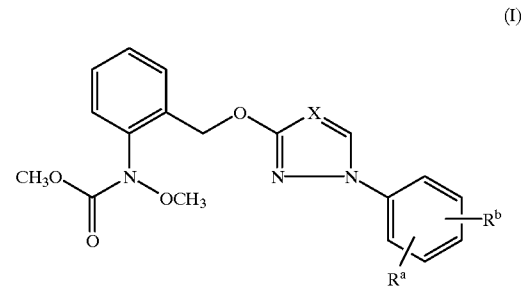

where
X is CH or N and
the radicals $R^a$ and $R^b$ independently of one another are a hydrogen atom, a halogen atom, a $C_1$–$C_4$-alkyl or a $C_1$–$C_4$-haloalkyl group; and b) at least one valine amide of the formula II

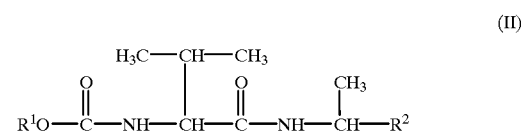

where
$R^1$ is $C_3$–$C_4$-alkyl and
$R^2$ is naphthyl or phenyl, the phenyl radical being substituted in the 4-position by a halogen atom, a $C_1$–$C_4$-alkyl group or $C_1$–$C_4$-alkoxy group.

2. A composition as claimed in claim 1, comprising at least one carbamate of formula I, where X has the abovementioned meaning and at least one of the radicals $R^a$ and $R^b$ is not a hydrogen atom.

3. A composition as claimed in any of the preceding claims, comprising at least one valine amide of the formula II where $R^1$ is i-propyl, sec-butyl or tert-butyl and $R^2$ is 4-Cl-, 4-methyl- or 4-methoxyphenyl, or 2-naphthyl.

4. A composition as claimed in claim 1, comprising at least one valine amide of the formula IIa

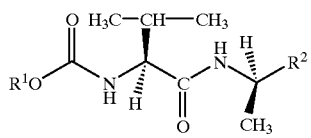

(IIa)

where $R^1$ and $R^2$ have the abovementioned meanings.

5. A composition as claimed in claim 1, wherein the weight ratio of the compound of formula I to the compound of formula II is 10:1 to 1:10.

6. A composition as claimed in claim 1, conditioned in two parts, the one part comprising the compound of formula I in a solid or liquid carrier and the other part comprising the compound of formula II in a solid or liquid carrier.

7. A composition as claimed in claim 1, wherein the weight ratio of the compound of formula I to the compound of formula II is 50:1 to 1:50.

8. A composition as claimed in claim 1, wherein the weight ratio of the compound of formula I to the compound of formula II is 25:1 to 1:20.

9. A composition as claimed in claim 1, wherein the weight ratio of the compound of formula I to the compound of formula II is 5:1 to 1:5.

10. A method of controlling harmful fungi, which comprises treating the harmful fungi, their environment, or the plants, seeds, soils, areas, materials or spaces to be kept free from them, with synergistically an effective amount of at least one composition as claimed in claim 1.

11. A method as claimed in claim 10, wherein at least one compound of formula I and at least one compound of formula II are applied simultaneously or in succession in any order.

* * * * *

UNITED STATES PATENT AND TRADEMARK OFFICE
CERTIFICATE OF CORRECTION

PATENT NO.    : 6,156,778
DATED         : December 5, 2000
INVENTOR(S)   : Mueller et al.

It is certified that error appears in the above-identified patent and that said Letters Patent is hereby corrected as shown below:

Title page,
Item [87], "May 3, 1998" should be -- May 5, 1998 --.

Column 18, claim 10,
Line 17, delete "an".

Signed and Sealed this

Twenty-fifth Day of September, 2001

Attest:

*Nicholas P. Godici*

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO. : 6,156,778
DATED : December 5, 2000
INVENTOR(S) : Mueller et al.

Page 1 of 1

It is certified that error appears in the above-identified patent and that said Letters Patent is hereby corrected as shown below:

Title page,
ABSTRACT,
After the last word "group" insert:
-- and to a method of controlling harmful fungi using these compositions --.

Column 3,
Line 17, "$C_1$-$C_4$-kaloalkyl" should be -- $C_1$-$C_4$-haloalkyl --.

Column 5,
Line 47, "3-methyl-1-pentenyl" should be -- 3-methyl-3-pentenyl --.

Column 7,
Line 40, delete the formula shown and substitute:

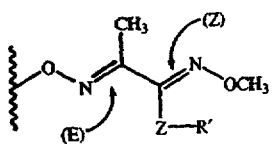

Column 17, claim 3,
Lines 5 and 6, delete "any of the preceding claims" and substitute -- claim 1 --.

Signed and Sealed this

Twenty-ninth Day of January, 2002

*Attest:*

*Attesting Officer*

JAMES E. ROGAN
*Director of the United States Patent and Trademark Office*